United States Patent [19]

Buser

[11] 4,185,500

[45] Jan. 29, 1980

[54] SAMPLE INTRODUCTION SYSTEM

[75] Inventor: Hansueli Buser, Arlesheim, Switzerland

[73] Assignee: Ciba-Geigy Corporation, Ardsley, N.Y.

[21] Appl. No.: 958,454

[22] Filed: Nov. 6, 1978

[30] Foreign Application Priority Data

Nov. 9, 1977 [CH] Switzerland ............... 13666/77

[51] Int. Cl.² .......................... G01N 1/10; G01N 1/22
[52] U.S. Cl. ............................................. 73/422 GC
[58] Field of Search ............ 73/422 GC, 23.1, 61.1 C

[56] References Cited

U.S. PATENT DOCUMENTS

| | | | |
|---|---|---|---|
| 3,205,711 | 9/1965 | Harris | 73/422 GC |
| 3,421,857 | 1/1969 | Reichle | 73/422 GC |
| 3,981,200 | 9/1976 | George | 73/422 GC |

FOREIGN PATENT DOCUMENTS 2530879 1/1976 Fed. Rep. of Germany .

OTHER PUBLICATIONS

Chromatography Newsletter, Article on pp. 21-24, vol. 5, No. 2, by Johansen et al.

*Primary Examiner*—S. Clement Swisher
*Assistant Examiner*—Denis E. Corr
*Attorney, Agent, or Firm*—Harry Falber

[57] ABSTRACT

A sample introduction system for a gas chromatograph having a chamber, a lock and a sample holder for introducing a sample via the lock into the chamber which has a needle for piercing the sample to allow a carrier gas introduced into the chamber access to the sample. The sample holder is hollow and has at that end remote from the end which holds the sample and communicating therewith, a pressure control valve so that a rise in pressure can be avoided as the sample is introduced into the lock and then the chamber.

6 Claims, 2 Drawing Figures

SAMPLE INTRODUCTION SYSTEM

FIELD OF THE INVENTION

This invention relates to a sample introduction system for a gas chromatograph, comprising a chamber provided with a receiving needle for sample capsules and a connection for a separating column, a lock upstream of the chamber, and a substantially rod-shaped sample holder, at one end of which a sample capsule can be fixed and by means of which the capsule can be introduced into the chamber through the lock.

PRIOR ART

A system of this kind is described, for example, in DOS No. 25 30 879 and is available from Messrs. Perkin-Elmer Corp. Norwalk, U.S.A., under the name MS 41.

As explained in DOS No. 25 30 879, undesirable excess pressures occur when the sample holder is introduced into the lock and into the chamber, and have a very disturbing effect particularly with capillary separating columns. DOS No. 25 30 879 proposes to obviate this problem by means of a pressure relief valve communicating with the lock, or by means of a pressure reducing valve in the carrier gas supply line.

SUMMARY OF THE INVENTION

It has now been found that the pressure surges due to the introduction of the sample holder can be obviated much more simply if, according to the invention, the sample holder is hollow and its end remote from the capsule is provided with a pressure control valve.

It has been found in practice that with the sample holder construction according to the invention practically absolutely constant pressure working conditions can be obtained. A preferred embodiment of the invention will be explained in detail below with reference to the drawings wherein:

DETAILED DESCRIPTION OF PREFERRED EMBODIMENT

Figure 1:
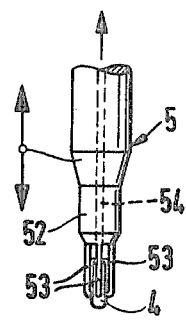
FIG. 1 is a section through a sample introduction system.
Figure 1:
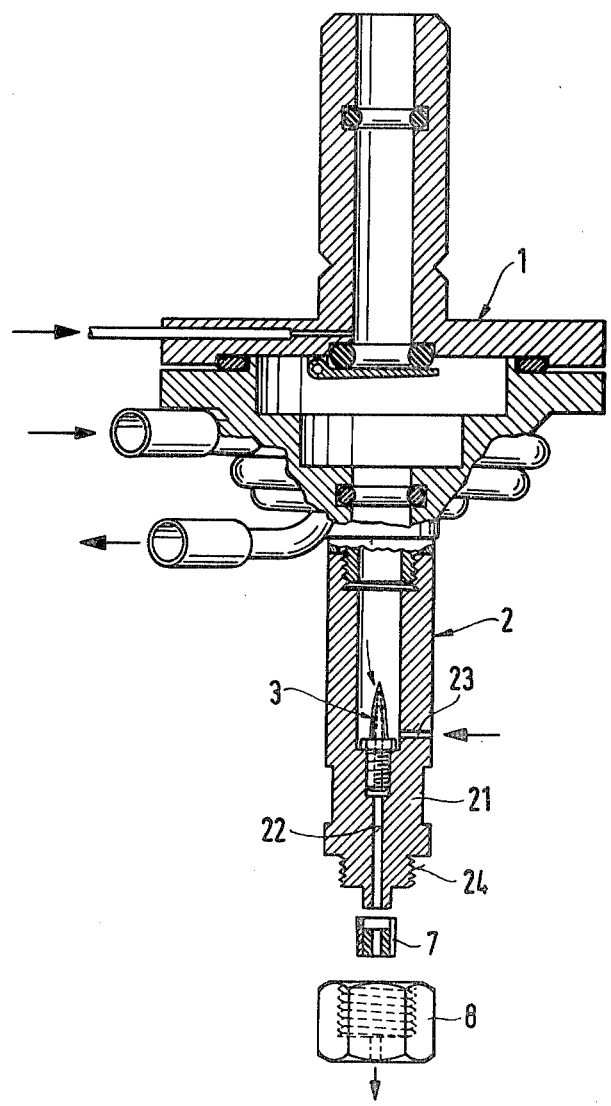

The sample introduction system shown in FIG. 1 comprises a lock 1 followed by a chamber 2 with a receiving needle 3 for a sample capsule 4 fixed at the bottom end of a sample holder 5 (shown only partially). Chamber 2 is bolted to the lock 1 in sealing-tight relationship. Needle 3 is screwed into the bottom part 21 of the chamber 2 which contains an axial passage 22 through which the top end of a separating column (not shown) is taken as far as or into the needle 3. A clamp sleeve 7 and a retaining nut 8 are provided to fix the column in the bottom part 21 and the nut 8 is adapted to be screwed on a matching thread 24 on the bottom part 21. 23 is a connection or inlet for carrier gas. Except for the chamber 2 and needle 3, which form the subject matter of our co-pending application Ser. No. 956,114, filed Oct. 30, 1978, and the sample holder 5 still to be described, other parts of the system illustrated are the same as those described in the above-mentioned Perkin-Elmer Corp. system MS 41 and DOS No. 25 30 879.

Figure 2:
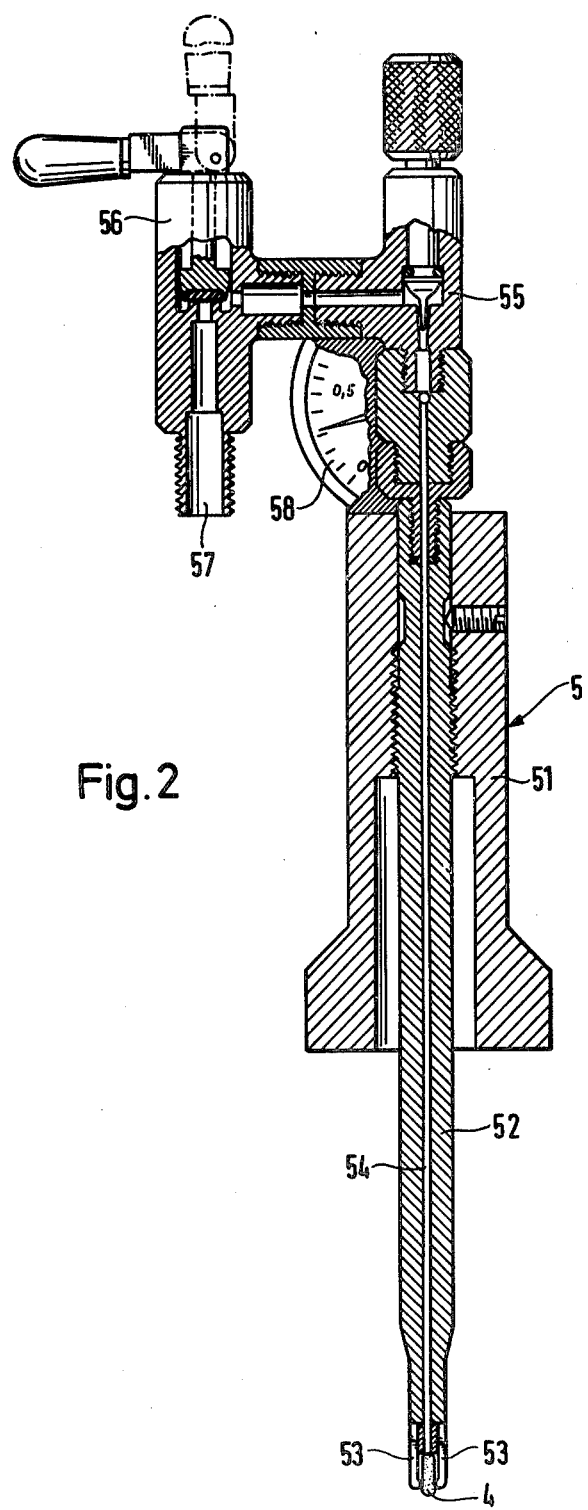
FIG. 2 is a capsule holder to an englarged scale.

Sample holder 5 is shown on an enlarged scale in FIG. 2. It comprises a tubular handle 51 in which a cylindrical rod 52 is disposed coaxially, its outside diameter corresponding to the inside diameter of the entry passage in the lock 1 and the chamber 2. The bottom end of the rod projecting from the handle is slotted and has four prongs 53 between which the sample capsule 4 is inserted and which then hold the latter resiliently. To this extent the sample holder 5 is in accordance with the prior art.

The novel feature is that the rod 52 is provided with a continuous axial passage 54 and a pressure control valve 55 connected to the passage 54 at the rod end remote from the capsule. A shut-off valve or cock 56 having an outlet 57 is connected to the pressure control valve. A pressure gauge 58 is also provided on the handle 51 to show the pressure in the passage 54.

When the sample holder 5 is introduced into the lock 1 and then into the chamber 2, the carrier gas can enter the passage 54 in the rod 52 between the prongs 53 and escape at a controlled rate via the needle valve 55 and the cock 56, which is open. A pressure rise during the introduction of the sample holder can be practically completely avoided by appropriate adjustment of the pressure control valve, which is advantageously constructed as a needle valve, so that constant pressure operating conditions are rendered possible. The cock 56 is closed immediately before the capsule is pierced by the needle 3.

I claim:

1. A sample introduction system for a gas chromatograph, comprising a chamber provided with a receiving needle for sample capsules and a connection for a separating column, a lock upstream of the chamber, and a substantially rod-shaped sample holder, at one end of which a sample capsule can be fixed and by means of which the capsule can be introduced into the chamber through the lock, wherein the sample holder is hollow and its end remote from the capsule is provided with a pressure control valve.

2. A system according to claim 1, including a shut-off valve connected to said sample holder.

3. A system according to claim 1, including an indicator for indicating the pressure in the hollow interior of the sample holder.

4. A system according to claim 2, including an indicator for indicating the pressure in the hollow interior of the sample holder.

5. A sample holder for a gas chromatograph comprising a hollow rod defining a passageway therethrough, means for holding at one end of said rod a sample, a pressure control valve mounted to that end of said rod remote from said one end and communicating with said passageway, a tubular handle in which said rod is mounted so that said one end of said rod extends beyond said handle and a pressure indicator connected to said handle to indicate the pressure in said passageway.

6. A sample holder according to claim 5, including a shut-off valve coupled to said pressure control valve.

* * * * *